US006468763B1

(12) United States Patent
Farinas

(10) Patent No.: US 6,468,763 B1
(45) Date of Patent: Oct. 22, 2002

(54) OPTICAL DETECTION OF TRANSMEMBRANE POTENTIAL CHANGES

(75) Inventor: Javier A. Farinas, San Carlos, CA (US)

(73) Assignee: Caliper Technologies Corp., Mountain View, CA (US)

( * ) Notice: Subject to any disclaimer, the term of this patent is extended or adjusted under 35 U.S.C. 154(b) by 133 days.

(21) Appl. No.: 09/661,337

(22) Filed: Sep. 14, 2000

Related U.S. Application Data

(60) Provisional application No. 60/156,639, filed on Sep. 29, 1999.

(51) Int. Cl.[7] .......................... C12Q 1/02; C12Q 1/00; C12N 13/00; G01N 33/53

(52) U.S. Cl. .......................... 435/29; 435/968; 435/4; 435/173.4; 436/63; 436/172

(58) Field of Search .......................... 435/29, 968, 4, 435/173.4; 436/63, 172

(56) References Cited

U.S. PATENT DOCUMENTS

| | | | |
|---|---|---|---|
| 5,278,048 A | 1/1994 | Parce et al. | |
| 5,496,697 A | 3/1996 | Parce et al. | |
| 5,661,035 A | 8/1997 | Tsien et al. | |
| 5,858,195 A | 1/1999 | Ramsey | |
| 5,942,443 A | 8/1999 | Parce et al. | |
| 6,046,056 A | 4/2000 | Parce et al. | |
| 6,107,066 A * | 8/2000 | Tsien et al. | 435/29 |

FOREIGN PATENT DOCUMENTS

| | | |
|---|---|---|
| WO | WO97/39008 | 10/1997 |
| WO | WO98/00231 | 1/1998 |

OTHER PUBLICATIONS

Cafiso, D.S. et al., "EPR Determination of Membrane Potentials," *Ann. Rev. Biophys. Bioeng.* (1981) 10:217–244.

Gonazlez, J.E. et al., "Voltage Sensing by Fluorescence Resonance Energy Transfer in Single Cells," *Biophys. J.* (1995) 69:1272–1280.

Gonzalez, J.E. et al., "Improved Indicators of Cell Membrane Potential that use Fluorescence Resonance Energy Transfer," *Chemistry & Biology* (1997) 4:269–277.

Jankowski, A. et al., "A noninvasive fluorimetric procedure for measurement of membrane potential," *J. Biol. Chem.* (1999) 26098–26104.

Leenhouts, J.M. et al., "Membrane potential–driven translocation of a lipid–conjugated rhodamine," *Biophys. Biochim. Acta* (1995) 1237:121–126.

(List continued on next page.)

*Primary Examiner*—Louise N. Leary
(74) *Attorney, Agent, or Firm*—Matthew B. Murphy

(57) ABSTRACT

Compositions for monitoring transmembrane potential across cellular membranes. The compositions typically comprise a cell having a plasma membrane that comprises a first leaflet and a second leaflet, the membrane comprising first and second membrane associated components which, when placed adjacent each other either produce or quench a fluorescent signal, wherein. The first membrane associated component translocates from a first leaflet of the membrane to a second leaflet of the membrane in response to an electrical potential gradient across the membrane, the first membrane associated component being selected from a non-fluorescent cationic fluorescence quencher a non-fluorescent anionic fluorescence quencher and a cationic fluorophore.

34 Claims, 6 Drawing Sheets

OTHER PUBLICATIONS

Loew, L.M. et al., "A Naphthyl Analog of the Aminostyryl Pryidinium Class of Potentiometric Membrane Dyes Shows Consistent Sensitivity in a Variety of Tissue, Cell, and Model Membrane Preparations," *J. membrane Biol.* (1992) 130:1–10.

Matko, J. et al., "Luminescence Quenching by Nitroxide Spin Labels in Aqueous Solution: Studies on the Mechanism of Quenching," *Biochem* (1992) 31:703–711.

Schroeder, K.S. et al., "FLIPR: A New Instrument for Accurate, High Throughout Optical Screening," *J. Biomol. Screen* (1999) 1:75–80.

Tanner, M.K. et al., "Flow Cytometric Analysis of Altered Mononuclear Cell Transmembrane Potential Induced by Cyclosporin," *Cytometry* (1993) 14:59–69.

Yguerabide, J., "Theory for Establishing Proximity Relations in Biological Membranes by Excitation Energy Transfer Measurements," *Biophys.J.* (1994) 66:683–693.

* cited by examiner

OPTICAL DETECTION OF TRANSMEMBRANE POTENTIAL CHANGES

CROSS REFERENCE TO RELATED APPLICATION

This application claims the benefit of U.S. Provisional Patent Application No. 60/156,639, filed Sep. 29, 1999, which is incorporated herein by reference in its entirety for all purposes.

BACKGROUND OF THE INVENTION

In biological and biochemical research, model systems are employed as screening tools to determine whether a given line of research will lead the investigator to the ultimately sought results, e.g., utility in medical, diagnostic or consumer applications, or the like. In order for these model systems to provide the most relevant information, it is often necessary for the model to come as close as possible to the ultimate application as is practical. In pharmaceutical research, the approximation of living systems has led to the substantial use of in vivo models, e.g., live animal testing, and pseudo-in vivo models, e.g., screening of living cell cultures in vitro, also termed cell-based assays.

Cell based assays are often preferred for initial screening assays due to their approximation of in vivo systems combined with their capability to be rapidly screened. Once a cellular system is selected as a model assay system, there is an additional problem of detecting the functioning of the cells in response to a particular stimulus. Specifically, most cellular responses of interest are not readily assayable by convenient means, e.g., using optical detection methods.

In order to address the detection problem, a number of solutions have been proposed. For example, one solution is to continually monitor the immediately surrounding environment of the cells for changes in pH, where the rate of pH change is related to the metabolic state of the particular cell. See, e.g., U.S. Pat. Nos. 5,278,048 and 5,496,697 to Parce et al. Alternative methods employ intracellular dyes which indicate levels of intracellular components, e.g., calcium, pH, and the like, and use those measurements as an indication of cellular functioning.

Another class of assays simply employs dyes that label internal components of the cells, e.g., nucleic acids. Upon cellular death, the integrity of the cellular membrane is compromised, leading to a leaking of the nucleic acids and dye. Thus, the presence of the dye within the cell is used as a measure of cellular viability.

In still another class of assays, the electrical potential gradient between the inside and the outside of a cell or of a cell compartment is used as an indication of the ion transport functions of cellular components. A variety of methods have been previously described for detecting transmembrane potentials in vesicles. Many of these methods, e.g., Biophys. Biochim. Acta 1237:121–126 (1995), Biophys. J. 71:2680–2691 (1996), and Ann. Rev. Biophys. Bioeng. 10:217–244 (1981), are not suitable for use with live cells in cell based assays because of nonspecific staining, toxicity, slow response time, or lack of sensitivity. Some methods have been described for detecting transmembrane potential in living cells. See, e.g., U.S. Pat. No. 5,661,035, and references cited therein, Biophys. J. 69:1272–1280 (1995), Chem Biol. 4:269–277 (1997), J. Biomol. Screen. 1:75–80 (1999), Cytometry 14:59–69 (1993) and J. Memb. Biol. 130:1–10 (1992).

Despite the availability of membrane potential sensor compositions and assays, there still exists a need for rapid detection of transmembrane potential in a readily automatable, high-throughput format. The present invention generally meets these and a variety of other needs.

SUMMARY OF THE INVENTION

The present invention provides compositions that are used in the detection of transmembrane potentials in living cells, methods of using these compositions in assaying biological function and in screening for effectors of that function, systems and microfluidic devices that use such compositions in performing these biological assays, and kits including these compositions. The compositions include first and second membrane associated components which produce or quench a fluorescent signal when adjacent to each other. The first component typically comprises a non-fluorescent anionic or cationic fluorescence quenching compound or a cationic fluorophore that translocates from one leaflet of the membrane to the other leaflet, in response to a change in transmembrane potential. The second component is disposed adjacent to or within one leaflet of the membrane and is selected from a fluorophore or a quencher, depending upon the nature of the first component. As a result, changes in transmembrane potential produce an increase or a decrease in the level of fluorophore quenching (or a decrease or increase in the amount of emitted fluorescence, respectively).

The present invention also provides methods of detecting transmembrane potential changes in a cell, kits for detecting transmembrane potential changes, and microfluidic devices and systems in which these methods may be carried out.

DETAILED DESCRIPTION OF THE INVENTION

Figure 1:
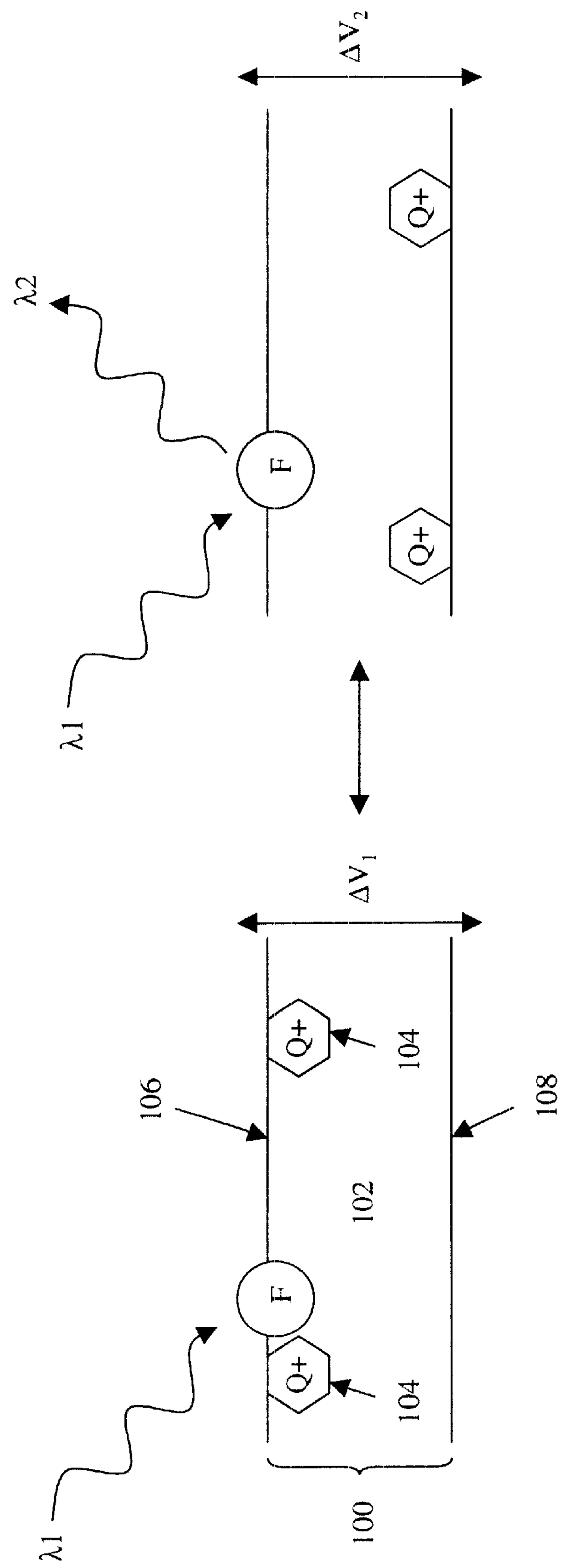
FIG. 1 schematically illustrates the functioning of the transmembrane potential sensing compositions of the present invention.

The present invention generally provides compositions, methods, kits and systems for measuring transmembrane potential, and changes in transmembrane potential brought on by external stimuli, e.g., chemical compounds, genetic elements, environmental conditions, and the like. In particular, the present invention in its various forms employs a transmembrane voltage sensing composition, which comprises a first and second membrane associated components. The two components are selected such that the ability of the two components either to produce a fluorescent signal or to quench an otherwise occurring fluorescent signal depends upon the proximity of the two components. By way of example, where one component comprises a fluorophore and the other comprises a fluorescence quenching compound, the close proximity of the two components results in the quenching of the fluorescent signal from the fluorophore. Fluorescence quenching can occur by a variety of mechanisms, including Forster-type resonance energy transfer, electron transfer, electron exchange, charge transfer and formation of ground state complexes (J. Biochem. 31:703–711 (1992) and Published International Patent Application No. WO 97/39008). In the case of fluorescent resonance energy transfer (FRET), proximity of the two components results in the production of a fluorescent signal that is not present, present to a lesser degree or present but with differing spectral characteristics, when the two components are not in close proximity.

When referring to proximity between two membrane associated components, the term adjacent or in close proximity refers to molecules that are sufficiently close to quench a fluorescent signal or for fluorescent resonance energy transfer. Typically such distances range from direct physical contact to about 100 angstroms, although precise distances may vary depending upon the nature of the assay conditions, reagents, etc.

This first membrane associated component is typically disposed between the inner and outer leaflets of a membrane, and translocates from a first leaflet of the membrane to a second leaflet of the membrane in response to changes in the electrical potential gradient across the membrane. The first component is typically selected from a non-fluorescent anionic or cationic quencher, or a cationic fluorophore.

The composition also typically includes a second component that includes a fluorophore or quencher asymmetrically associated with the membrane such that the concentration of the component in or adjacent to the first leaflet is greater than the concentration in or adjacent to the second leaflet. Where the first and second components are a fluorophore-quencher pair, the fluorophore is quenched by the quencher to a greater extent when the two components are predominantly in or adjacent to the same leaflet than when the two components are in or adjacent to different leaflets of the membrane. Thus, depending upon the direction of translocation of the first component which is in turn, dependent upon the net charge of the translocating component, and the location of the second component, e.g., inner membrane leaflet or outer membrane leaflet, the fluorophore emits fluorescence (when excited) when the transmembrane potential increases or decreases. Thus, the compositions of the present invention produce a detectable change in fluorescence in response to a change in transmembrane potential. This change can be an increase or decrease in the fluorescence or a change in the spectral characteristics of the composition depending upon a number of factors that are described in greater detail below.

FIG. 1 is a schematic illustration of one example of the functioning of certain embodiments of the voltage sensing compositions of the present invention, e.g., where the first component comprises a cationic quencher and the second component comprises a fluorophore. As shown, under a first transmembrane potential $\Delta V_1$, a first component 104 that comprises a non-fluorescent fluorescence quenching ion (indicated by Q+) is adjacent to or within one leaflet 106 of the membrane 100. A fluorophore (indicated by F) is also located adjacent to the same membrane leaflet 108 under the particular transmembrane potential, such that the proximity of the quencher is close enough to quench the fluorophore. As indicated, light of wavelength $\lambda_1$ is absorbed by the fluorophore while no light is emitted. Under a different transmembrane potential, indicated by $\Delta V_2$, the quencher ion 104 translocates across the membrane 100 to the opposite leaflet 108 of the membrane 100 from the fluorophore 102. As a result of the translocation, the quencher 104 is no longer sufficiently proximal to the fluorophore 102 to quench the fluorescence, and light or fluorescence of wavelength $\lambda_2$ is emitted. As noted, the direction of translocation of the quencher ion depends upon the nature of the change in transmembrane potential, e.g., the direction of the voltage gradient, as well as the nature of the charge of the quenching ion, e.g., anionic or cationic in the particular environment. Although illustrated with a cationic translocating quencher, it will be appreciated that the other aspects of the present invention, e.g., translocating non-fluorescent anions, or cationic fluorophores, operate in substantially the same manner.

I. Voltage Sensing Composition

As noted above, the voltage sensing composition used in accordance with the present invention includes a first ionic component that translocates from one face of a cellular membrane to the other face of the membrane in response to a transmembrane potential or voltage gradient. The composition also includes a second component that is located within or adjacent to one leaflet of the cellular membrane, e.g., the inner or outer leaflet. Together, these two components comprise a fluorophore-quencher pair.

As noted above, the first component is generally a non-fluorescent anionic or cationic fluorescence quencher, or a cationic fluorophore. The ionic nature of the first component enables the translocation of this component under a transmembrane potential gradient. In particular, when a voltage gradient is present across the membrane, the charged first component redistributes in accordance with the Nernst equation. In particularly preferred aspects, anionic translocating components are preferred for their faster rate of translocation relative to cationic components.

In one aspect of the present invention, the first or translocating membrane associated component is a non-fluorescent cationic or anionic fluorescence quencher component. As used herein, the "quencher" component describes a group, which functions to quench the fluorescence of a fluorophore by any of a number of different mechanisms including Forster-type fluorescence resonance energy transfer (FRET), electron transfer, electron exchange, charge transfer and formation of a dark complex. Where quenching occurs by FRET, the quencher acts as a dark acceptor. Because the quencher is non-fluorescent, it does not emit light as a result of FRET.

A variety of different quencher components are optionally employed as the first or translocating component of the present invention. For example, particularly suitable non-fluorescent cationic quenchers include, e.g., crystal violet, malachite green derivatives, methylene blue, dabcyl labeled 1-aminobutyltriphenylphosphonium bromide, CAT 16, tempo, proxyl or doxyl labeled 1-aminobutyltriphenylphosphonium bromide. Suitable non-fluorescent anionic quenchers include, e.g., spin labeled fatty acids, i.e., 5-doxylstearic acid, trinitrophenol spin labels, brominated lipids, i.e., 9-bromostearic acid and tetraaryl borates.

As noted above, where the first or translocating component is a non-fluorescent quencher, the second component is a fluorophore that is quenched by the quencher. To a certain extent, therefore, the nature of the quencher as the first component depends upon the nature of the fluorophore chosen as the second component, and vice versa. Specifically, quencher/fluorophore pairs are typically selected to be compatible, with the pairs being chosen such that redistribution or translocation of the quencher across the membrane is efficiently converted to changes in the level of quenching of the fluorophore. A variety of different quencher-fluorophore pairs are well known in the art. See, e.g., Lachowicz, Principles of Fluorescence Spectroscopy (1983).

In addition to the characteristic of being able to interact with the second component, the first or translocating component typically includes additional elements that allow it to function in accordance with the invention described herein. In particular, the first translocating component typically comprises a hydrophobic moiety that allows it to interact with the cell membrane in the capacity desired, e.g., within or associated with the membrane. By way of example, with respect to the quencher components described above, the quencher component optionally includes a hydrophobic group, e.g., large hydrocarbon moieties ($C_3$ to $C_{20}$). See, e.g., U.S. Pat. No. 5,661,035, which is incorporated herein by reference for all purposes.

In alternate aspects, the first or translocating component is a cationic fluorophore. As used herein, a "fluorophore" refers to a compound that is itself fluorescent. Where the first or translocating component is a fluorophore, the second component comprises a quencher. A large variety of cationic fluorophores may be used in accordance with this aspect of the present invention. For example, particularly suitable cationic fluorophores include, e.g., octadecyl rhodamine, carbocyanine derivatives, i.e., DiOC7(3), DiSC3(5), DiI, DiO, DiD, styryl derivatives, i.e., Rh-413, FM-464, dodecyl resorufin, 1-pyrenebutyltriphenyl phosphonium bromide, and bodipy labeled triphenylphosphonium bromide.

Previous work has ignored the importance of the location of the second component in maximizing the voltage dependent signal generated by the translocation of the first component (See, e.g., U.S. Pat. No. 5,661,035). Theoretical considerations show that the location of the second component (inner versus outer leaflet) affects the efficiency with which the voltage dependent translocation of ions is converted into a fluorescence response. This can be seen by noting that the concentration of a translocating ion is given by the Nernst equation and the change in fluorescence signal caused by the interaction of the translocating ion and the stationary second member is approximately defined by a Stern-Volmer relation: $Io/I=1+KC_s$ where $C_s$ is the concentration of the translocating member at the leaflet where the stationary member is located, K is a constant which depends on the nature of the interaction between the components, I is the fluorescence intensity and Io is the fluorescence intensity in the absence of an interaction between the two components (Biophys. J., 66:683–693, 1994). Combining these equations, the dependence of the fluorescent signal on the charge of the translocating ion and the location of the second member can be derived. For a cationic translocating ion, the voltage dependence of the fluorescence signal is given by $I/Io=(1+K\,C_t/(1+10^{(-V/60)}))^{-1}$ for a second member on the external leaflet and by $I/Io=(1+K\,C_t/(1+10^{(V/60)}))^{-1}$ for a second member on the inner leaflet where $C_t$ is the total concentration of the translocating ion and V is the transmembrane voltage (mV). For an anionic translocating ion, the voltage dependence of the fluorescence signal is given by $I/Io=(1+K\,C_t/(1+10^{(V/60)}))^{-1}$ for a second member on the external leaflet and by $I/Io=(1+K\,C_t/(1+10^{(-V/60)}))^{-1}$ for a second member on the inner leaflet. The sensitivity of the fluorescence signal to changes in voltage can be obtained from the derivative of the fluorescence intensity with respect to voltage. For cationic translocating ions at a given value of I/o, the ratio of the sensitivity for an external second component compared to the sensitivity for an internal second component is equal to $(1+10^{(-V/60)})/(1+10^{(V/60)})$ which is greater than one for V<0 mV. For anionic translocating ions at a given value of I/Io, the ratio of the sensitivity for an external second component compared to the sensitivity for an internal second component is equal to $(1+10^{(V/60)})/(1+10^{(-V/60)})$ which is less than one for V<0 mV. For an external second component, the ratio of the sensitivity for a cationic translocating ion compared to the sensitivity for an anionic translocating ion is equal to $(1+10^{(V/60)})/(1+10^{(V/60)})$ which is greater than one for V<0 mV. For cell based assays, one typically deals with cells whose resting potential is negative inside (V<0 mV). Under these conditions, cationic quenchers are used with greater sensitivity when the second member is located on the outer leaflet; anionic quenchers are used with greater sensitivity when the second member is located on the inner leaflet and cationic quenchers are more sensitive than anionic quenchers when the second member is located on the outer leaflet. High sensitivity allows small voltage changes to be measured accurately.

The compositions used in accordance with the present invention also include a second membrane associated component which is localized on or within the cellular membrane in such a fashion that the combination of the first and second membrane associated components yields a fluorescent signal that is dependent upon the transmembrane potential condition. Thus, the pair of the first and second components, when subjected to a first transmembrane potential are in sufficient proximity such that in the case of a fluorophore-quencher pair, the fluorescence is quenched, or in the case of a FRET pair, fluorescence energy is transferred from the donor component to the acceptor component. Under a different transmembrane potential, the first and second components are dislocated from each other such that the above-described interaction does not occur, thus giving rise to a fluorescence signal or removing a FRET signal.

Accordingly, the second membrane associated component is typically asymmetrically located adjacent to or within one of the leaflets of the membrane, but not the other leaflet, thereby permitting a differential signal indicative of the relative position of the two components. By "asymmetrically located" is meant that a substantial majority of the second component in the membrane composition is located adjacent to or within one membrane leaflet and not the other, such that the relative position of the first or translocating component can be readily determined via the resulting fluorescent signal or lack of signal. Typically, at least 75% of the second membrane associated component is located adjacent or within one of the membrane leaflets, preferably, at least 80% of the second membrane associated component, and more preferably, at least 90% of the second membrane associated component is adjacent to one membrane leaflet. In particularly preferred aspects, the majority of the second membrane associated component in the composition is located within or adjacent to the outer leaflet of a cell membrane, due to the relative ease of configuring the asymmetrically located component in this fashion, e.g., it is simpler to selectively coat an outer membrane leaflet than an inner membrane face.

As noted above with respect to the first component of the compositions described herein, the nature of the second membrane associated component is selected to be compatible with the first membrane associated component, in order to provide a sufficient level of fluorescent signal. For example, where the first translocating component comprises a quencher, the second membrane associated component typically comprises a fluorescent compound that is quenched by the first component when the two components are in sufficient proximity. Similarly, where the first translocating component comprises a fluorescence donor of a FRET pair, then the second membrane associated components comprise the fluorescence acceptor of the pair. Still further, in the instance where the first translocating component is a fluorophore, the second component may comprise a quencher of that fluorophore, or a fluorescence acceptor or donor of a FRET pair of which the first component is the complementary member.

A variety of different compounds may be employed as the second membrane associated component. For example, fluorescent components useful in accordance with the present invention include, e.g., green fluorescent protein (GFP) mutants, fluorescein DHPE, tetramethylrhodamine DHPE, bodipy DHPE, texas red DHPE, β-$C_8$-bodipy-$C_5$-HPC, NBD-labeled lipids, fluorescent lectins (i.e., fluorescein WGA, Rhodamine WGA), lipophilic fluorescent dextrans (i.e., fluorescein lipophilic dextran, tetramethylrhodamine lipophilic dextran), and fluorescently labeled 'anti-surface epitope' antibodies.

In the case where the first or translocating component is a cationic fluorophore, suitable quenchers are typically selected from brominated lipids, spin labeled lipids, malachite green labeled lipids, and the like.

As with the first translocating component, the second component also will typically comprise a hydrophobic moiety or include a binding region to ensure localization, adsorption or binding of this component to the desired leaflet, e.g., the outer leaflet, of the plasma membrane. Such hydrophobic moieties include those described above. Binding functionalities may generally be selected from those regions or moieties that are known in the art, including, e.g., lectins for binding cell surface carbohydrates, antibody or antibody fragments that bind cell surface epitopes, ligands that bind cell surface receptors, and the like.

In the case where the second membrane associated component comprises a fluorophore, typically, it would be expected that fixing the fluorophore component on one leaflet of the membrane, e.g., extracellular, rather than providing the fluorophore as the intramembrane component, would lead to background fluorescence levels that are too high. For example, in U.S. Pat. No. 5,661,035, it was stated that in the case of impermeant dyes or fluorophores, e.g., those localized on the extracellular leaflet of a plasma membrane, "a significant fraction of the total dye signal comes from molecules that sit on irrelevant membranes or cells and that dilute the signal from the few correctly placed molecules." In particular, because location of the fluorophore component would be expected to be easier than location of the intramembrane component, one would expect the levels of the fluorophore to be substantially higher than the levels of quencher, thus leading to excessively high levels of background fluorescence, even when the intramembrane quenchers are located adjacent the leaflet of the membrane at which the fluorophores are located. Surprisingly, however, the use of such systems is not believed to carry with it excessive background fluorescence levels, and in fact, provides more than adequate signal to noise levels.

Although generally described in terms of a separate membrane associated components, it will be appreciated that the first membrane associated component, also termed the translocating component and the second membrane associated component may be linked as separate domains in the same molecule via a linker group. Specifically, the linker group ensures efficient cooperation between the first and second components in the generation or quenching of a fluorescent signal. A variety of acceptable linker groups may be employed in accordance with the present invention. Examples include, e.g., bi-functionalized polyethylene (polybutylene, polyproplyene), glycol PEG oligomers, e.g., of approximately 8–10 monomer units in length, and the like. These and other linkers are described in U.S. Pat. No. 5,661,035, which is incorporated herein by reference for all purposes.

Alternatively, although described as a single quencher component and a single fluorophore component, it will also be appreciated that the present invention contemplates a composition that includes at least two different fluorophore components which distribute to different faces of the membrane from each other, and fluoresce at different wavelengths or are quenched to a different extent. Such compositions are optionally employed for obtaining ratiometric measurements of membrane potential. Similarly, different quencher molecules are optionally employed within a single membrane, which different quenchers translocate in opposite directions in response to a particular potential and quench to a different extent, or quench different fluorophore components, such that a multicolor system can be employed for detection of transmembrane potential. For example, a membrane that employs a first quencher/fluorophore pair that emits at a first wavelength and a second quencher/fluorophore pair that emits at a second wavelength emits a different wavelength depending upon the direction of change in transmembrane potential. By determining which fluorophore is emitting and which is quenched, one can more accurately measure the transmembrane potential change. Further, by selecting a number of such pairs, one can provide a single composition that can be used to measure transmembrane potential changes over a wide range of different conditions.

The compositions of the present invention typically include the membrane component across which a voltage gradient is to be measured. Although membrane preparations may be used in accordance with the present invention, in order to maximize the relevance of a given assay, it is typically preferred to use whole, viable cell systems. Accordingly, the compositions of the present invention are typically incorporated within and comprise the plasma membrane of a viable cell population, and/or organelle membranes within a living cell. The nature of the cell population that is part of this composition typically depends upon the type of assay that is to be performed. For example, if one is seeking to assay the effects of environmental conditions on mammalian cell systems, then a mammalian cell culture that incorporates the elements of the present invention is used. Similarly, for bacterial or fungal assays, appropriate cell cultures again are used. In general, any number of different cell cultures may be used in accordance with the present invention, including mammalian, bacterial, fungal, plant, insect, and the like. Because of their relevance for pharmaceutical research for human and veterinary therapeutics, mammalian cells are typically most preferred. Examples of suitable mammalian cell lines include, e.g., CHO, HEK, as well as other well-characterized mammalian cell lines.

II. Assay Methods

In addition to voltage sensing compositions, the present invention also provides methods of utilizing those compositions in assays of cellular or other functions. In particular, the present invention provides a method of detecting a change in transmembrane potential. In these methods, a composition is used which provides a fluorescent signal in response to a change in a potential gradient across the membrane, as described above. As noted above, the composition is typically provided in the context of a viable whole cell and/or cell culture. Also as noted above, the fluorescent signal may be characterized in a number of ways, including an increase in fluorescence, a decrease in fluorescence, a change in the ratio of fluorescent emissions at different wavelengths, and the like.

In accordance with the methods of the invention, the change in the level of fluorescence of the composition is then detected, where the change in fluorescence is indicative of a change in transmembrane potential. Typically, the assay methods described herein are used to detect the effect of some stimulus on the functioning of a cellular system. Where one is seeking to determine the effect of some stimulus on a cell's transmembrane potential, e.g., through a change in ion flux, transport, membrane permeability, or the like, one need only expose the cell to that stimulus and examine the cell for the presence of a previously absent fluorescent signal (or the absence of a previously present fluorescent signal). Of particular interest are the effects of chemical compounds, e.g., drug candidates, on cellular functioning.

The assay methods typically comprise the step of providing an appropriate voltage sensing composition, as described above. As noted, these compositions are usually embodied in a viable cell population which has the voltage sensing composition integrated with its plasma membranes and/or organelle membranes. In accordance with these methods, the cell population of the present invention is typically placed into a reaction vessel, and the level of fluorescence from the population is measured. This provides an initial or background level of fluorescence indicative of the existing transmembrane potential for the cell population. The particular stimulus that is to be tested is then inflicted upon the cell population. For example, a pharmaceutical candidate or test compound is added to the cell population. Following this stimulus, the fluorescence level of the cells is again measured and compared to the initial fluorescent level or the fluorescence level in a control cell population. Any change in the level of fluorescence not attributable to the dilution from the test compound (as determined from an appropriate control) is then attributable to the effect the test compound has on the cell's transmembrane potential.

As described in greater detail below, typically, these types of reactions are carried out in an appropriate reaction receptacle that allows measurement of fluorescence, in situ. As such, the receptacle is typically a transparent reaction vessel, such as a test tube, a reaction well in a multiwell plate, or a transparent conduit, e.g., a capillary, microchannel or tube. In particularly preferred aspects, the assay methods are carried out in the channel or channels of a microfluidic device, as described in greater detail below.

In preferred aspects, the compositions of the present invention employ additional fluorescent labels that serve as a reference label. The use of these reference labels permits flowing assays, e.g., in microfluidic systems, that do not require single cell isolation or sorting for detection. The use of dual label, e.g., reference label and function labels for cell based assays is described in detail in U.S. Patent Application Ser. No. 09/104,519 filed Jun. 25, 1998, which is incorporated herein by reference for all purposes.

The assay methods of the present invention are particularly useful in performing high-throughput (greater than 1,000 compounds/day) and even ultra-high throughput (e.g., greater than 10,000 compounds/day) screening of chemical libraries, e.g., in searching for pharmaceutical leads. These experiments may be carried out in parallel by a providing a large number of reaction mixtures (e.g., cell suspensions as described herein) in separate receptacles, typically in a multiwell format, e.g., 96 well, 324 well or 1536 well plates. Different test compounds (library members) are added to separate wells, and the effect of the compound on the reaction mixture is ascertained, e.g., via the fluorescent signal. These parallelized assays are generally carried out using specialized equipment to enable simultaneous processing of large numbers of samples, i.e., fluid handling by robotic pipettor systems and fluorescent detection by multiplexed fluorescent multi-well plate readers.

In an alternative aspect, the assays are carried out, at least in part, in a serial format, where separate samples are screened one after another for an effect on a cellular system. In order to expand throughput, these individual serial processing units themselves may be multiplexed or parallelized. In particularly preferred aspects, the serial assays are performed within a microfluidic device or system. Examples of these microfluidic devices and systems are described in Published International Patent Application No. WO 98/00231, which is incorporated herein by reference in its entirety for all purposes.

III. Assay Systems

The present invention also provides assay systems for carrying out the assay methods of the present invention. Briefly and as noted above, such systems typically employ a reaction or assay receptacle in which the compositions of the invention are disposed. Additional reagents may be added, e.g., as potential or actual inhibitors or enhancers of the reaction of interest. Typically, the receptacle includes at least a portion that is transparent, so that the fluorescent signal from the voltage sensing composition may be detected. Of course, in the case of test tubes or wells, detection can be made through an opening in the receptacle, e.g., the top opening of a well. A variety of receptacles are useful in the present invention, including individual test tubes, cuvettes, wells in a multiwell plate, or capillary tubes.

Figure 2A:
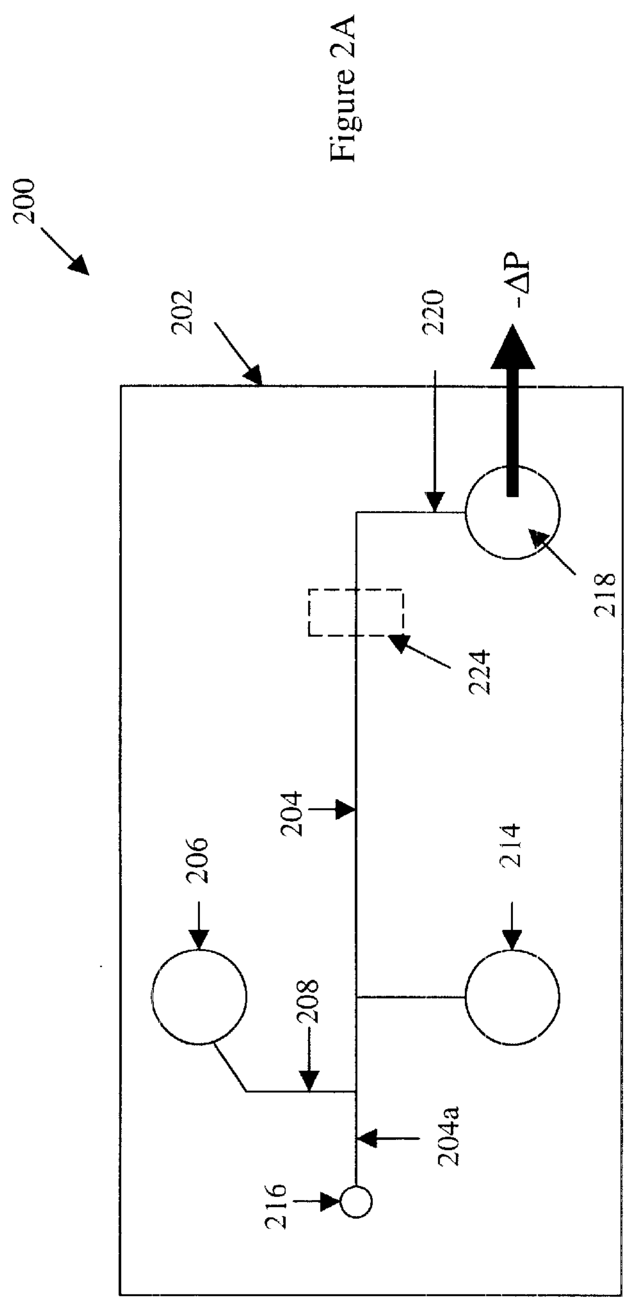
FIG. 2 schematically illustrates a microfluidic device used in practicing certain embodiments of the present invention.
Figure 2B:
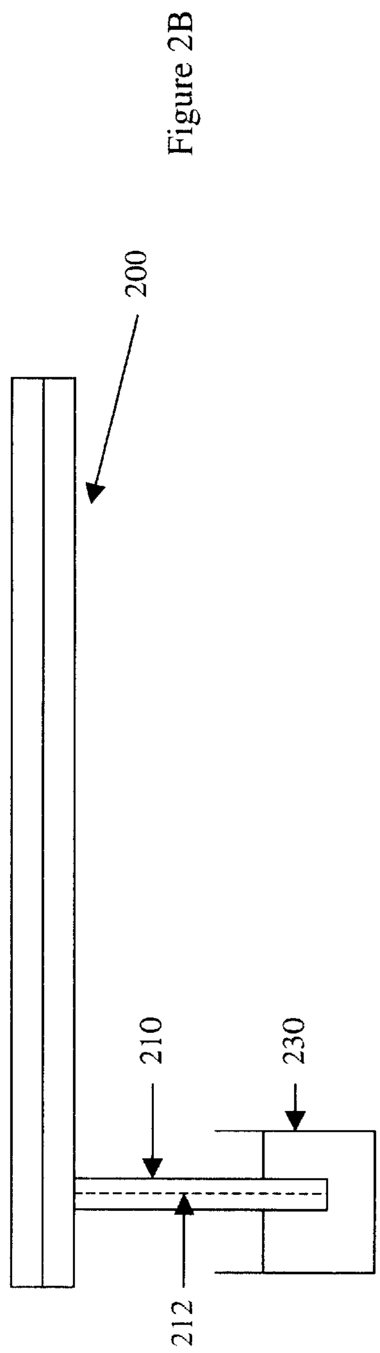

In many aspects, it is preferred to use a microscale fluidic channel, e.g., in the context of a channel network of a microfluidic device as the receptacle. Typically, these microfluidic devices include a body structure having at least a first main channel disposed therein. The first main channel typically includes a detection zone through which the fluorescent signals of the voltage sensing composition may be detected, e.g., at least a portion of the main channel that is transparent. A source of a cellular membrane that includes the voltage sensing components of the compositions described herein is also provided fluidly connected to the first channel. Typically, this source of cellular material comprises a well or reservoir that is fluidly connected to the main channel via a connecting channel portion. In the case of screening assay applications, the main assay channel is typically provided fluidly connected or connectable to a plurality of sources of different test compounds that are to be screened. One example of a microfluidic device for carrying out these methods is schematically illustrated in FIG. 2.

As shown, the device 200 includes a body structure 202 which has a main channel 204 disposed within its interior. Typically, such channels are produced as grooves in the surface of a planar substrate layer, over which is bonded an additional substrate layer which seals the channel between the two layers. Such devices are described in, e.g., U.S. patent application Ser. No. 09/14,519, incorporated herein by reference. The main channel 204 is shown in fluid communication with reservoir 206, which functions as the source of cellular suspension. The reservoir is fluidly connected to the main channel 204 via channel portion 208. Optional additional reservoir(s) 214 is also shown in fluid communication with main channel 204. The optional additional reservoir(s) may be used for additional reagents, diluents or the like that are used in the assay. Main channel 204 is also shown in fluid communication with an external sampling capillary element 210. Specifically, capillary element 210 has an interior capillary channel 212. The capillary element 210 is joined with the body 202 of the device 200 such that the capillary channel 212 is in fluid communication with the main channel 204, e.g. at junction 216. This is typically accomplished by providing an opening in the body 202 into which is inserted the capillary element 210. The opening in the body 202 is positioned such that the capillary channel communicates with the main channel 204 of the device 200.

For microfluidic applications, the systems of the present invention typically include material transport systems for flowing the cellular suspension through the main channel of the device, and for periodically introducing a test compound into the main channel. A variety of different material transport systems may be employed in this respect. For example, in preferred cases, the material transport system relies upon the application of a pressure differential across the length of the channels through which fluid movement is desired. Such systems may employ a number of pressure and/or vacuum sources that are applied at the termini of various channels of the device to create pressure differentials through those channels. In preferred aspects, however, a single vacuum source is applied to a common waste reservoir, e.g., waste reservoir 218, as shown by the "$-\Delta P$", in FIG. 2. This vacuum source creates a simultaneous pressure differential across the length of all of the interconnected channels of the system, to draw materials into and through those channels, and into the main channel. Differential volume or rate of flow of different fluids into the main channel is typically accomplished by providing selected resistances to the channels intersecting the main channel. These resistances are generally varied by varying the cross sectional dimensions and/or lengths of these channels, as described in, e.g., U.S. patent application Ser. No. 09/238,467 filed Jan. 28, 1999, which is incorporated herein by reference for all purposes.

Alternatively, controlled electrokinetic material transport systems may be employed. Examples of such transport systems are described in, e.g., U.S. Pat. No. 5,858,195, and U.S. patent application Ser. No. 09/104,519, already incorporated herein. Such systems utilize electric fields applied across the various channels to generate fluid or material movement through those channels in accordance with the current level flowing through the channel.

Because the compositions of the present invention produce fluorescent signals as an indication of the reaction of interest, such systems also typically include a fluorescence detection system that is in sensory communication with the reaction receptacle. One example of a fluorescence detection system is described and illustrated in the U.S. patent application Ser. No. 09/104,519, incorporated supra. By "in sensory communication" is meant that the detector is oriented with respect to the reaction receptacle such that it is capable of receiving a fluorescent signal produced from the contents of the reaction receptacle. Typically this involves the placement of the detector over a transparent or open region of the receptacle such that collection optics of the detector are focused on the transparent region for collecting fluorescence emitted from the receptacle.

In operation, the systems of the present invention are particularly useful for the high-throughput screening assays that are also described above. In particular, a suspension of cells that embodies the compositions described herein, is flowed along main channel 204 from reservoir 206. Optional additional reagents, e.g., buffer, diluents and the like, are flowed into main channel 204 from optional reservoir(s) 214. External capillary element 210 is periodically placed into contact with fluid in a sample well 230, e.g., in a multiwell plate, to draw up a volume of test compound. The volume of test compound is the flowed up the channel 212 in capillary element 210 and into main channel 204 (through junction 216) whereupon it mixes with the cell suspension. The effect of these test compounds on the transmembrane potential in the cell suspension is then detected downstream at detection window 224, via an appropriate fluorescence detector.

In optional aspects, additional channels (not shown) may be provided intersecting the main channel 204 on opposite sides of the channel, immediately upstream of detection window 224 (with reference to the direction of flow of material, cells and/or fluids). The purpose of such channels is to provide an influx of fluid into the main channel 204 that focuses the cell suspension in the center of the main channel 204 at the detection point 224 to ensure more accurate detection of individual cells and their responses.

Figure 3:
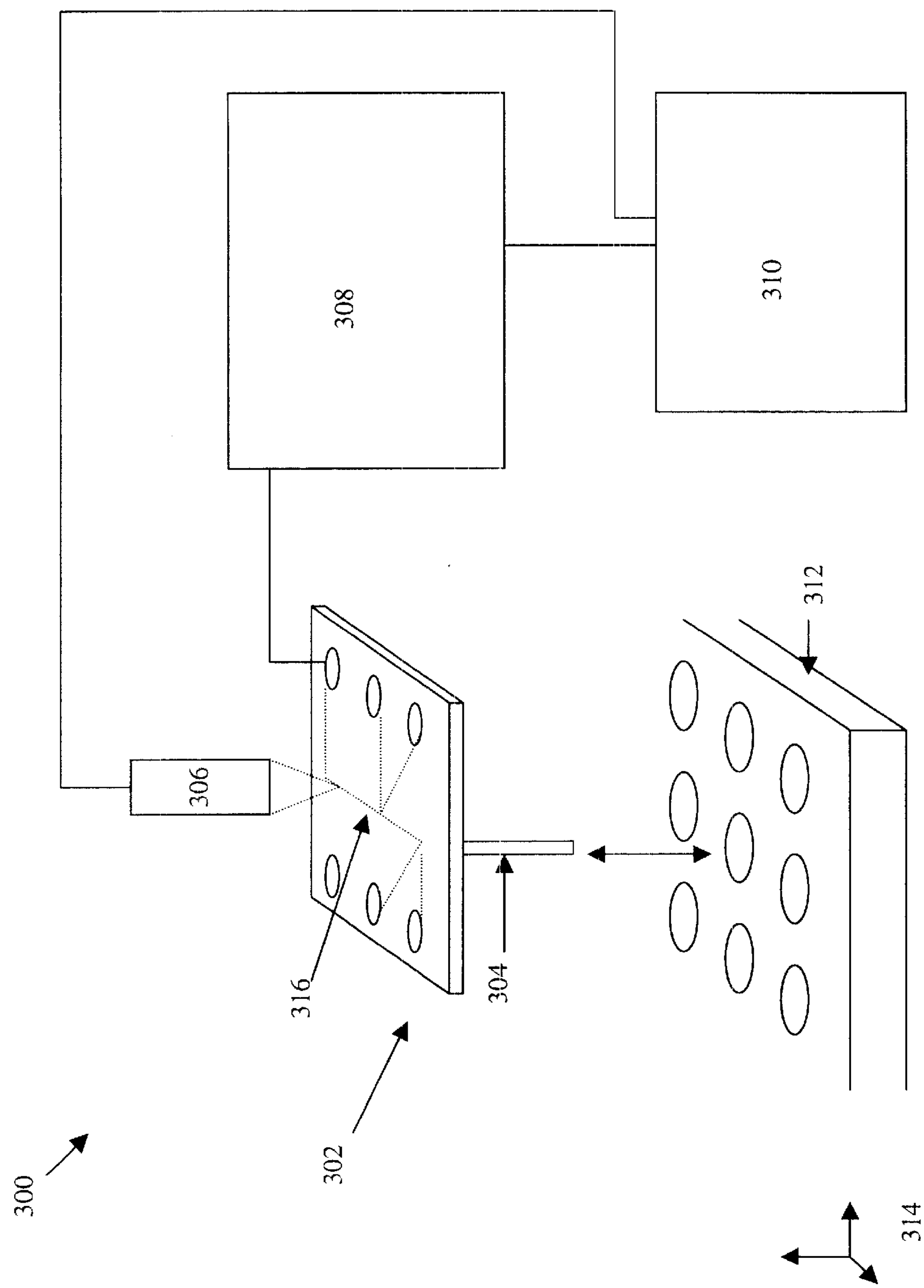
FIG. 3 schematically illustrates an example of an overall integrated system used to practice the present invention.

A schematic illustration of an overall integrated assay system according to the present invention is illustrated in FIG. 3. As shown, the system 300 includes a reaction receptacle, illustrated as microfluidic device 302 (including optional capillary element 304 and channel network 316, disposed in the device), a detector 306 disposed in sensory communication with the reaction receptacle, and optional material transport system 308 for directing flow of materials through the microfluidic device 302 and computer 310, for recording and analyzing data received from the detector 306 as well as instructing or controlling the operation of the material transport system 308. Also shown is a test compound library, e.g., plate 312, the individual components of which are screened for effects upon the functioning of cellular compositions as described herein. One or both of the device 302 and the library plate may be mounted upon an x-y-z translation stage 314, in order to permit accession of different samples on the plate 314 by the microfluidic device 302.

In operation, reagents for the particular assay to be performed (e.g., cells incorporating the voltage sensing compositions described herein) by the device 302 are flowed through the channel network 316 and past the detector 306. A number of different test compounds are serially introduced into the channel network 316 from plate 314 (via capillary 304), where they mix with the cell suspension in the channel network. Upon flowing past the detector, any effect that the test compounds have upon the transmembrane potential of the cells is detected by the detector by virtue of the presence of the voltage sensing composition within the cells. In particular, the transmembrane potential is measured in the absence of the test compound, and re-measured in the presence of the test compound. A change in the potential indicates that the test compound has an effect upon the transmembrane potential of the cells, as described previously. Typically, the overall screening assay is set up as a continuous flow assay, e.g., as described in Published International Patent Application No. WO 98/00231, incorporated by reference herein. Briefly, the cellular suspension is transported past the detector where a constant background signal (e.g., steady state) is measured that is indicative of the normal transmembrane potential signal level from the cells that are to be assayed. When an effector of the transmembrane potential of the cells is introduced to the cellular suspension and flowed past the detector 306, it produces a deviation in the steady state signal from the cells, which is then readily detected and identified, e.g., by the computer 310.

IV. Assay Kits

The present invention also provides kits for carrying out the assay methods described herein. In particular, these kits typically include the compositions described herein, as well as additional components to facilitate the performance of the assay methods by an investigator. In particular, the kits typically comprise the voltage sensing composition of the invention which includes a cellular membrane having a first leaflet and a second leaflet, where the membrane includes a first membrane associated component which comprises a fluorescence quenching ion which translocates from the first leaflet of the membrane to the second leaflet of the membrane in response to an electrical potential gradient across the membrane. The kit also includes a second component asymmetrically located adjacent to one of the first and second leaflets of the membrane. Optionally, the second component is either a quencher or a fluorophore such that the fluorescence emitted from the first or second components depends upon their proximity, as described in substantial detail above. Optionally, the first and second components are provided within the kit separate from the membrane component, but with appropriate instructions and reagents for placing these elements in the appropriate positions relative to the membrane before the assay is performed.

The kit also typically includes a receptacle in which the assay reaction is carried out. As noted herein, the reaction receptacle is optionally a reaction vessel, i.e., a test tube or well in a multiwell plate, or a channel or chamber region within a microfluidic device. The reaction receptacle is also typically transparent, at least in part, in order to detect the fluorescent signals from the reaction mixture.

The elements of the kits of the present invention are typically packaged together in a single package. The package optionally includes other reagents used in the assay, e.g., buffers, standard reagents, and the like, as well as written instructions for carrying out the assay in accordance with the methods described herein. In the case of prepackaged reagents, the kits optionally include pre-measured or predosed reagents that are ready to incorporate into the assay methods without measurement, e.g., pre-measured fluid aliquots, or pre-weighed or pre-measured solid reagents that may be easily reconstituted by the end-user of the kit.

V. EXAMPLES

The present invention is further illustrated by the following non-limiting examples:

A. Example 1

Use of Crystal Violet as a Non-Fluorescent Cationic Translocating Quencher in Sensing Transmembrane Potential Crystal violet was purchased from Fischer Scientific. Fluorescein labeled wheat germ agglutinin (WGA-F1) was purchased from Sigma Chemical. Valinomycin was purchased from Sigma Chemical Chinese hamster ovary cells (CHO) were grown in Ham's F12 media (Irvine Scientific) with 10% fetal bovine serum and 1% penicillin/streptomycin. Adherent cells were harvested using phosphate buffered saline with 0.5 mM EDTA (Irvine Scientific). Cells were washed in Hank's buffered saline solution (HBSS) containing 20 mM Hepes at pH 7.2. Cells suspended in HBSS at a concentration of $10^6$ cells/ml were stained with 2 μg/ml WGA-F1 and 40 nM crystal violet for 15 minutes at room temperature. The cells were washed with HBSS and suspended in HBSS containing 1 μM sulforhodamine 101 (Sigma Chemical). Sulforhodamine 101 was used as a voltage insensitive volume marker to account for possible dilution artifacts. Transmembrane voltage was varied by suspending cells in solutions of varying potassium concentration in the presence of 5 μM valinomycin to establish a potassium diffusion potential. Cells suspended in high sodium buffer ( 6 mM K+) were hyperpolarized (transmembrane voltage~−80 mV) while cells suspended in high potassium buffer (126 mM K+) were depolarized (transmembrane voltage~5 mV). Fluorescence measurements on cell suspensions were made at room temperature using a FluoroMax-2 fluorometer (Spex). Excitation was at 475 nm using 4 nm excitation and emission slit widths.

Figure 4:
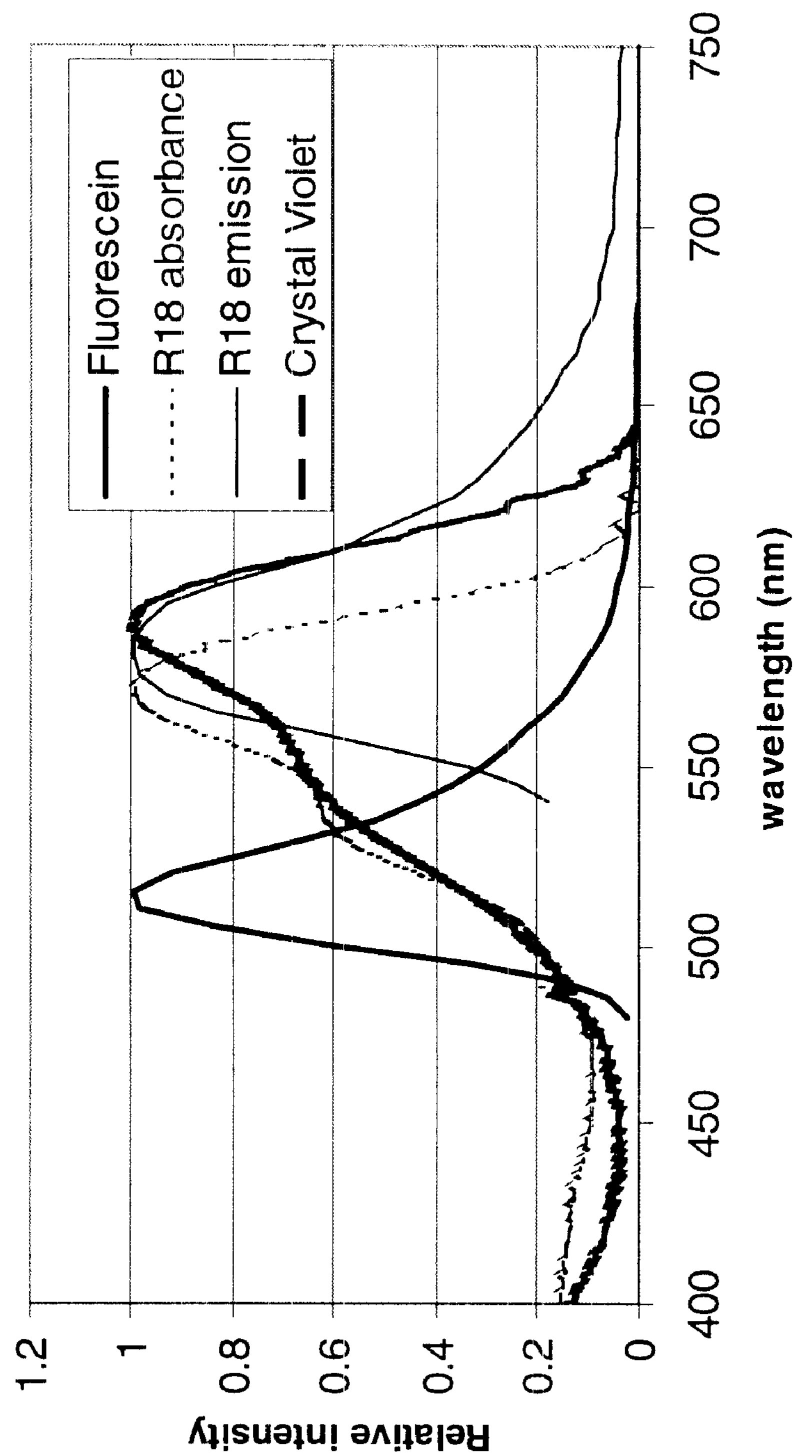
FIG. 4 shows normalized spectra for fluorescein emission, R18 absorbance and emission and crystal violet absorbance.

Crystal violet was chosen as a membrane-translocating, non-fluorescent, cationic, fluorescence quencher based on its hydrophobicity, delocalized positive charge and large extinction coefficient with significant overlap of its absorption band with the emission of fluorescein (see FIG. 4). WGA-F1 was chosen as the asymmetric fluorescent donor since it labels the extracellular face of the plasma membrane.

Figure 5:
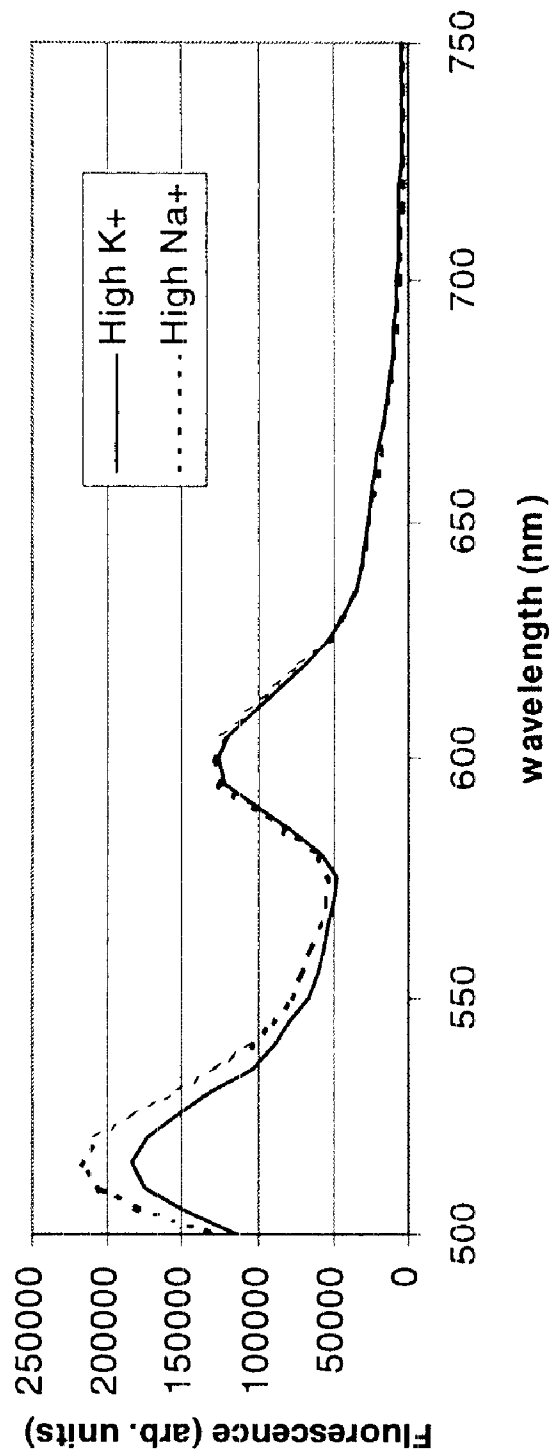
FIG. 5 shows the voltage dependent quenching of WGA-F1 fluorescence by. crystal violet in response to changes in the potassium diffusion potential.

As shown in FIG. 2, the distribution of membrane-bound cationic quencher depends on the transmembrane voltage in accordance with the Nernst equation. The cationic quencher will redistribute from the intracellular side of the plasma membrane to the extracellular side as the cell is depolarized. The redistribution decreases the average distance between the cationic quencher and the fluorophore bound to the extracellular side of the plasma membrane. This results in greater quenching of the fluorophore. The fluorescence signals for labeled CHO cells suspended in high sodium and high potassium buffers are shown in FIG. 5. The fluorescein fluorescence in the depolarized cells is decreased by 20% compared to the hyperpolarized cells. No difference is seen in sulforhodamine 101 fluorescence. When suspended in the same buffers, cells labeled with only WGA-F1 showed no significant change in the fluorescein fluorescence.

B. Example 2

Use of Octadecyl Rhodamine 18 (R18) as a Fluorescent Cationic Translocating Quencher in Sensing Transmembrane Potential Octadecyl rhodamine B (R18) was purchased from Molecular Probes. Cells were grown as described in example 1. Cells suspended in HBSS at a concentration of $10^6$ cells/ml were stained with 2 μg/ml WGA-F1 and 500 nM R18 for 15 minutes at room temperature. The cells were washed with HBSS and suspended in HBSS. Transmembrane voltage was varied as described in example 1. Fluorescence measurements on cell suspensions were made at room temperature using a FluoroMax-2 fluorometer (Spex). Excitation was at 475 nm using 4 nm excitation and emission slit widths.

R18 was chosen as a membrane-translocating, fluorescent, cationic, fluorescence quencher based on its hydrophobicity, delocalized positive charge and large extinction coefficient with significant overlap of its absorption band with the emission of fluorescein (see FIG. 4). The ability to detect sensitized emission from R18 allows a ratiometric measurement of voltage-dependent quenching. WGA-F1 was chosen as the asymmetric fluorescent donor since it labels the extracellular face of the plasma membrane.

Figure 6A:
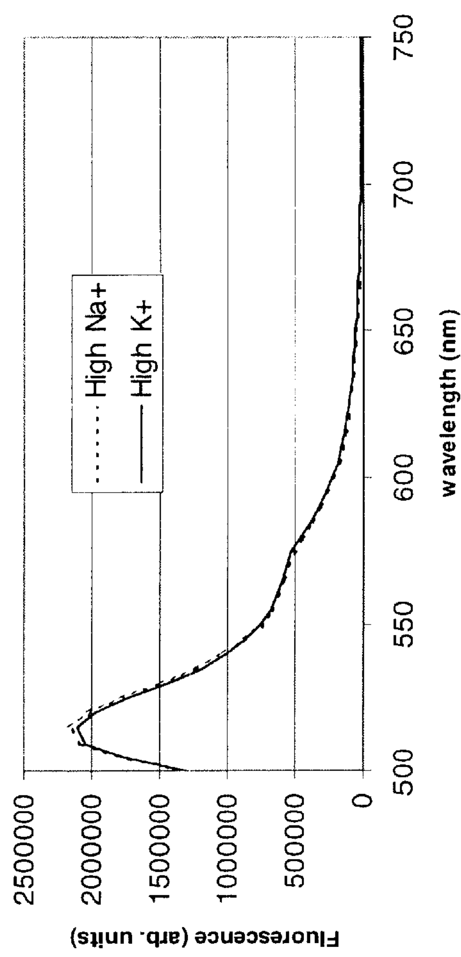
FIG. 6 shows the voltage dependent quenching of WGA-F1 fluorescence by R18 in response to changes in the potassium diffusion potential. The fluorescence signals for labeled CHO cells suspended in high sodium and high potassium buffers are shown in FIG. 6*a*. The difference between the high sodium and high potassium spectra are shown in FIG. 6*b*.
Figure 6B:
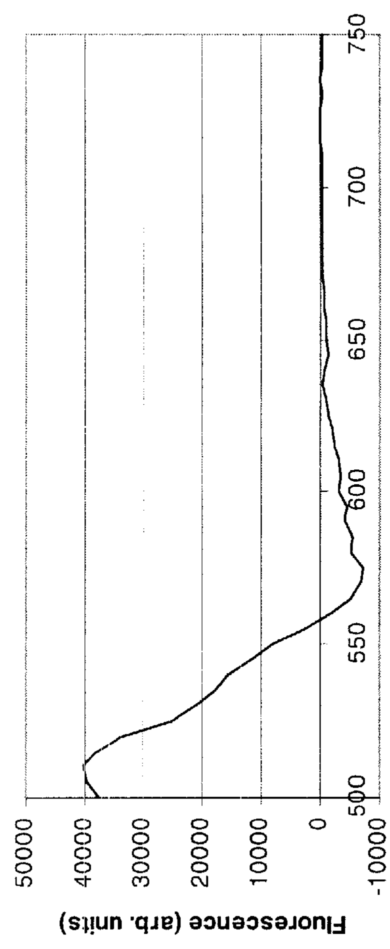

As shown in FIG. 2, the distribution of membrane-bound cationic quencher depends on the transmembrane voltage in accordance with the Nernst equation. The cationic quencher redistributes from the intracellular side of the plasma membrane to the extracellular side as the cell is depolarized. The redistribution decreases the average distance between the cationic quencher and the fluorophore bound to the extracellular side of the plasma membrane. This results in greater quenching of the fluorophore and higher sensitized emission from the translocating fluorophore. The fluorescence signals for labeled CHO cells suspended in high sodium and high potassium buffers are shown in FIG. 6*a*. The difference between the high sodium and high potassium spectra are shown in FIG. 6*b*. The fluorescein fluorescence in the depolarized cells is decreased by 3% and the rhodamine fluorescence is increased by 2% compared to the hyperpolarized cells. The observed changes in fluorescein and R18 fluorescence are consistent with the translocation-dependent changes in fluorescence resonance energy transfer.

All publications and patent applications are herein incorporated by reference to the same extent as if each individual publication or patent application was specifically and individually indicated to be incorporated by reference. Any concentration values provided in the above-description and appended claims refer to concentrations on an admixed basis without regard to any conversion, derivatization, complexing or dissociation in the resulting mixture. Although the present invention has been described in some detail by way of illustration and example for purposes of clarity and understanding, it will be apparent that changes and modifications may be practiced yet still fall within the scope of the appended claims.

What is claimed is:

1. A transmembrane voltage sensing composition, comprising:

a viable cell having a plasma membrane;

first and second membrane associated components associated with the plasma membrane which, when placed adjacent to each other either produce or quench a fluorescent signal, wherein:

the first membrane associated component translocates from a first leaflet of the membrane to a second leaflet of the membrane in response to an electrical potential gradient across the membrane, the first membrane associated component being selected from a non-fluorescent cationic fluorescence quencher, a non-fluorescent anionic fluorescence quencher and a cationic fluorophore; and the second membrane associated component is asymmetrically located adjacent to one of the first and second leaflets of the membrane, wherein the second membrane component is selected from a fluorophore and a quencher.

2. The composition of claim 1, wherein the first membrane associated component comprises a cationic fluorophore, and wherein the second membrane associated component is asymmetrically located adjacent an outer leaflet of the plasma membrane.

3. The composition of claim 1, wherein the first membrane associated component comprises a non-fluorescent anionic quencher and the second component is asymmetrically located adjacent an interior face of the plasma membrane.

4. The composition of claim 1, wherein the first component comprises a non-fluorescent cationic fluorescence quencher selected from crystal violet, malachite green derivatives, methylene blue, dabcyl labeled 1-aminobutyltriphenylphosphonium bromide, CAT 16, tempo, and proxyl or doxyl labeled 1-aminobutyltriphenylphosphonium bromide.

5. The composition of claim 1, wherein the first component comprises a non-fluorescent anionic fluorescence quencher selected from spin labeled fatty acids, trinitrophenol spin labels, brominated lipids, and tetraaryl borates.

6. The composition of claim 1, wherein the first component comprises a cationic fluorophore selected from octadecyl rhodamine, carbocyanine derivatives, styryl derivatives, dodecyl resorufin, 1-pyrenebutyltriphenyl phosphonium bromide, and bodipy labeled triphenylphosphonium bromide.

7. The composition of claim 1, wherein the first and second components are connected by a linker group.

8. The composition of claim 1, wherein the cell is selected from mammalian, bacterial, fungal, insect and plant cells.

9. The composition of claim 8, wherein the cell comprises a mammalian cell.

10. The composition of claim 9, wherein the mammalian cell is selected from a CHO, and a HEK cell.

11. A method of detecting a change in transmembrane potential, comprising:

providing a viable cell that comprises a plasma membrane having a first face and a second face, said membrane comprising first and second membrane associated components which, when placed adjacent each other either produce or quench a fluorescent signal, wherein:

the first membrane associated component translocates from a first face of the membrane to a second face of the membrane in response to an electrical potential gradient across the membrane, the first membrane associated component being selected from a non-fluorescent cationic fluorescence quencher a non-fluorescent anionic fluorescence quencher and a cationic fluorophore; and the second membrane associated component is asymmetrically located adjacent to one of the first and second faces of the membrane, wherein the second membrane component is selected from a fluorophore and a quencher; and detecting a change in a level of fluorescence of one of the first and second membrane associated components, the change in fluorescence being indicative of a change in transmembrane potential.

12. The method of claim 11, further comprising exposing the cell to one or more test compounds prior to the detecting step, the detecting step detecting a change in transmembrane potential in response to the test compound.

13. The method of claim 12, wherein the exposing and detecting steps are repeated, serially, with a plurality of different test compounds.

14. The method of claim 13, wherein the exposing and detecting steps are carried out in a microchannel, the viable cell flowing through the channel in a stream.

15. The method of claim 11, wherein in the providing step, the first membrane associated component comprises a cationic fluorophore, and wherein the second membrane associated component is asymmetrically located adjacent an outer leaflet of the plasma membrane.

16. The method of claim 11, wherein in the providing step, the first membrane associated component comprises a non-fluorescent anionic quencher and the second component is asymmetrically located adjacent an interior face of the plasma membrane.

17. The method of claim 11, wherein in the providing step, the first membrane associated component comprises a non-fluorescent cationic fluorescence quencher selected from crystal violet, malachite green derivatives, methylene blue, dabcyl labeled 1-aminobutyltriphenylphosphonium bromide, CAT 16, tempo, and proxyl or doxyl labeled 1-aminobutyltriphenylphosphonium bromide.

18. The method of claim 11, wherein in the providing step, the first membrane associated component comprises a non-fluorescent anionic fluorescence quencher selected from spin labeled fatty acids, trinitrophenol spin labels, brominated lipids, and tetraaryl borates.

19. The method of claim 11, wherein in the providing step, the first membrane associated component comprises a cationic fluorophore selected from octadecyl rhodamine, carbocyanine derivatives, styryl derivatives, dodecyl resorufin, 1-pyrenebutyltriphenyl phosphonium bromide, and bodipy labeled triphenylphosphonium bromide.

20. The method of claim 11, wherein in the providing step, the first and second membrane associated components are connected by a linker group.

21. The method of claim 11, wherein the biological cell provided in the providing step is selected from mammalian, bacterial, fungal, insect and plant cells.

22. The method of claim 11, wherein the biological cell provided in the providing step comprises a mammalian cell.

23. The method of claim 22, wherein the mammalian cell is selected from a CHO, and a HEK cell.

24. A kit for measuring transmembrane potential, comprising:

a cell having a plasma membrane having a first leaflet and a second leaflet, first and second membrane associating components which, when placed adjacent each other either produce or quench a fluorescent signal, wherein:

the first membrane associating component is capable of translocating from a first leaflet of the membrane to a second leaflet of the membrane in response to an electrical potential gradient across the membrane, the first membrane associating component being selected from a non-fluorescent cationic fluorescence quencher a non-fluorescent anionic fluorescence quencher and a cationic fluorophore; and the second membrane associating component is capable of being asymmetrically located adjacent to one of the first and second leaflets of the membrane, wherein the second membrane component is selected from a fluorophore and a quencher;

a transparent reaction receptacle; and instructions for carrying out the method of claim 11, wherein the cellular membrane, the reaction receptacle and the instructions are packaged together.

25. A kit for measuring transmembrane potential, comprising:

a cell having a plasma membrane having a first leaflet and a second leaflet, the membrane comprising first and second membrane associated components which, when placed adjacent to each other either produce or quench a fluorescent signal, wherein:

the first membrane associated component translocates from a first leaflet of the membrane to a second leaflet of the membrane in response to an electrical potential gradient across the membrane, the first membrane associated component being selected from a non-fluorescent cationic fluorescence quencher a non-fluorescent anionic fluorescence quencher and a cationic fluorophore; and the second membrane associated component is asymmetrically located adjacent to one of the first and second leaflets of the membrane, wherein the second membrane component is selected from a fluorophore and a quencher;

a transparent reaction receptacle; and instructions for carrying out the method of claim 11, wherein the cellular membrane, the reaction receptacle and the instructions are packaged together.

26. A microfluidic device for measuring transmembrane potential, comprising:

a body structure having at least a first channel disposed therein, the first channel including a detection zone;

a source of a cellular membrane fluidly connected to the first channel, which cellular membrane comprises a first leaflet and a second leaflet, said membrane comprising first and second membrane associated components which, when placed adjacent each other either produce or quench a fluorescent signal, wherein:

the first membrane associated component translocates from a first leaflet of the membrane to a second leaflet of the membrane in response to an electrical potential gradient across the membrane, the first membrane associated component being selected from a non-fluorescent cationic fluorescence quencher a non-fluorescent anionic fluorescence quencher and a cationic fluorophore; and the second membrane associated component is asymmetrically located adjacent to one of the first and second leaflets of the membrane, wherein the second membrane component is selected from a fluorophore and a quencher; and a material transport system for moving the cellular membrane composition through the first channel, and through the detection zone.

27. The microfluidic device of claim 26, wherein the body structure comprises a planar element having the at least first channel disposed within an interior portion of the planar element.

28. The microfluidic device of claim 27, wherein the planar element comprises at least first and second planar layers having first and second facing surfaces, respectively, the first channel being defined as a groove in at least one of the first and second facing surfaces, whereby mating of the first facing surface to the second facing surface encloses the groove to define the first channel.

29. The microfluidic device of claim 28, wherein the body structure is fabricated from a solid substrate selected from glass, silicon, quartz, and a polymeric solid substrate.

30. The microfluidic device of claim 29, wherein the body structure comprises glass.

31. The microfluidic device of claim 29, wherein the body structure is fabricated from a polymeric solid substrate selected from polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, and ABS (acrylonitrile-butadiene-styrene copolymer).

32. The microfluidic device of claim 26, wherein the material transport system comprises a pressure or vacuum source connected to at least one end of the first channel to generate a pressure differential across a length of the first channel, the pressure differential causing movement of the cellular membrane through the first channel.

33. The microfluidic device of claim 26, wherein the first channel comprises a transparent region for transmitting a fluorescent signal from the cellular membrane.

34. The microfluidic device of claim 33, further comprising a fluorescence detector disposed adjacent and within sensory communication of the transparent region for detecting a fluorescence signal from the cellular membrane.

* * * * *